(12) United States Patent
Ishibashi et al.

(10) Patent No.: US 8,323,892 B2
(45) Date of Patent: Dec. 4, 2012

(54) HYBRIDIZATION METHOD AND APPARATUS

(75) Inventors: Tohru Ishibashi, Tokyo (JP); Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 214 days.

(21) Appl. No.: 12/671,202

(22) PCT Filed: Aug. 8, 2007

(86) PCT No.: PCT/JP2007/065894
§ 371 (c)(1),
(2), (4) Date: Jan. 28, 2010

(87) PCT Pub. No.: WO2009/016770
PCT Pub. Date: Feb. 5, 2009

(65) Prior Publication Data
US 2010/0209925 A1 Aug. 19, 2010

(30) Foreign Application Priority Data
Aug. 2, 2007 (JP) ................. 2007-201716

(51) Int. Cl.
*C12Q 1/68* (2006.01)
*C12M 1/00* (2006.01)
*C12M 1/34* (2006.01)
*C12M 3/00* (2006.01)
*C07H 21/02* (2006.01)
*C07H 21/04* (2006.01)

(52) U.S. Cl. .... 435/6.1; 536/23.1; 536/24.3; 435/283.1; 435/287.2

(58) Field of Classification Search .................. None
See application file for complete search history.

(56) References Cited

U.S. PATENT DOCUMENTS

| | | | |
|---|---|---|---|
| 6,365,375 B1 | 4/2002 | Dietmaier et al. | |
| 2004/0110278 A1 | 6/2004 | Okano et al. | |
| 2004/0235032 A1 | 11/2004 | Suzuki et al. | |
| 2004/0241643 A1 | 12/2004 | Yamamoto et al. | |
| 2005/0106613 A1 | 5/2005 | Ishibashi | |
| 2007/0003446 A1 | 1/2007 | Takahata et al. | |
| 2007/0104619 A1 | 5/2007 | Ishibashi et al. | |
| 2007/0184479 A1 | 8/2007 | Nozato | |
| 2008/0194413 A1* | 8/2008 | Albert .............. | 506/1 |
| 2010/0041165 A1 | 2/2010 | Ishibashi et al. | |

FOREIGN PATENT DOCUMENTS

| | | |
|---|---|---|
| DE | 197 50 237 A1 | 5/1999 |
| EP | 0 235 727 A2 | 9/1987 |
| EP | 0 957 177 A2 | 11/1999 |
| EP | 1 447 454 A1 | 8/2004 |
| EP | 1 752 534 A1 | 2/2007 |
| EP | 1 775 589 A1 | 4/2007 |
| JP | 2004-298017 A | 10/2004 |
| JP | 2005-162 A | 1/2005 |
| JP | 2005-328709 A | 12/2005 |
| JP | 2006-47153 A | 2/2006 |
| JP | 3746756 B2 | 2/2006 |
| JP | 2007-14351 A | 1/2007 |
| WO | 98/08973 A1 | 3/1998 |
| WO | 01/06016 A2 | 1/2001 |
| WO | 03/020952 A2 | 3/2003 |

OTHER PUBLICATIONS

Liu, Y. et al., Anal. Chem., vol. 74, pp. 3063-3070 (2002).*
Gyllensten, U.B. et al., PNAS USA, vol. 85, pp. 7652-7656 (1988).*
European Search Report dated Dec. 12, 2011 in European Application No. 07792534.5.
PCT International Search Report and Written Opinion of the International Searching Authority, International Application No. PCT/JP2007/065894, Mailing Date Oct. 9, 2007.
Dietmaier, et al., "Multiple Mutation Analyses in Single Tumor Cells with Improved Whole Genome Amplification", American Journal of Pathology, vol. 154, No. 1, Jan. 1999, pp. 83-95.

* cited by examiner

*Primary Examiner* — Teresa E Strzelecka
(74) *Attorney, Agent, or Firm* — Fitzpatrick, Cella, Harper & Scinto

(57) ABSTRACT

A target nucleic acid contained in a sample solution is hybridized with a probe nucleic acid capable of binding specifically to the target nucleic acid and immobilized on a substrate. The process includes hybridizing the target nucleic acid with the probe nucleic acid, collecting the sample solution that has undergone the hybridization, amplifying the target nucleic acid contained in the collected sample solution, and hybridizing the amplified nucleic acid with the probe nucleic acid.

7 Claims, 5 Drawing Sheets

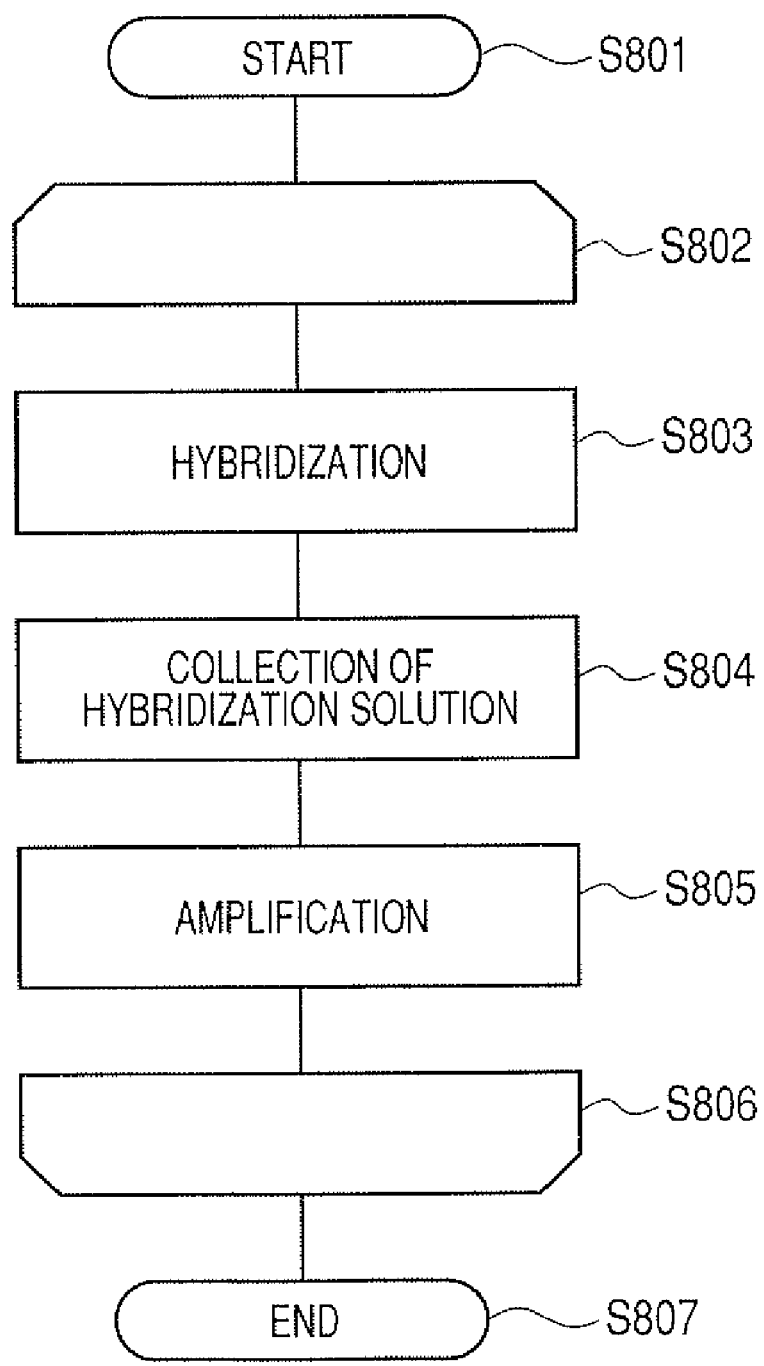

SEQUENCE LISTING

<160> NUMBER OF SEQ ID NOS: 11

<210> SEQ ID NO 1
<211> LENGTH: 23
<212> TYPE: DNA
<213> ORGANISM: Enterobacter cloacae

<400> SEQUENCE: 1
gtagcacaga gagcttgctc tcg                                          23

<210> SEQ ID NO 2
<211> LENGTH: 23
<212> TYPE: DNA
<213> ORGANISM: Artificial
<220> FEATURE:
<223> OTHER INFORMATION: PCR primer

<400> SEQUENCE: 2
gcggcgtgcc taatacatgc aag                                          23

<210> SEQ ID NO 3
<211> LENGTH: 23
<212> TYPE: DNA
<213> ORGANISM: Artificial
<220> FEATURE:
<223> OTHER INFORMATION: PCR primer

<400> SEQUENCE: 3
gcggcaggcc taacacatgc aag                                          23

<210> SEQ ID NO 4
<211> LENGTH: 23
<212> TYPE: DNA
<213> ORGANISM: Artificial
<220> FEATURE:
<223> OTHER INFORMATION: PCR primer

<400> SEQUENCE: 4
gcggcaggct taacacatgc aag                                          23

<210> SEQ ID NO 5
<211> LENGTH: 22
<212> TYPE: DNA
<213> ORGANISM: Artificial
<220> FEATURE:
<223> OTHER INFORMATION: PCR primer

<400> SEQUENCE: 5
atccagccgc accttccgat ac                                           22

<210> SEQ ID NO 6
<211> LENGTH: 22
<212> TYPE: DNA
<213> ORGANISM: Artificial
<220> FEATURE:
<223> OTHER INFORMATION: PCR primer

```
<400> SEQUENCE: 6
atccaaccgc aggttcccct ac                                              22

<210> SEQ ID NO 7
<211> LENGTH: 22
<212> TYPE: DNA
<213> ORGANISM: Artificial
<220> FEATURE:
<223> OTHER INFORMATION: PCR primer

<400> SEQUENCE: 7
atccagccgc aggttcccct ac                                              22

<210> SEQ ID NO 8
<211> LENGTH: 8
<212> TYPE: DNA
<213> ORGANISM: Artificial
<220> FEATURE:
<223> OTHER INFORMATION: Model probe

<400> SEQUENCE: 8 cgtacgta                                                               8

<210> SEQ ID NO 9
<211> LENGTH: 21
<212> TYPE: DNA
<213> ORGANISM: Artificial
<220> FEATURE:
<223> OTHER INFORMATION: Model Target

<400> SEQUENCE: 9
tacgttacgt acgggaagta g                                               21

<210> SEQ ID NO 10
<211> LENGTH: 24
<212> TYPE: DNA
<213> ORGANISM: Artificial
<220> FEATURE:
<223> OTHER INFORMATION: Model Target

<400> SEQUENCE: 10
ttatacgtta cgtacgggaa gtag                                            24

<210> SEQ ID NO 11
<211> LENGTH: 5
<212> TYPE: DNA
<213> ORGANISM: Artificial
<220> FEATURE:
<223> OTHER INFORMATION: Model Probe

<400> SEQUENCE: 11 cgtat                                                                  5
```

HYBRIDIZATION METHOD AND APPARATUS

TECHNICAL FIELD

The present invention relates to a method and an apparatus for detecting the amount or presence or absence of a target nucleic acid through the hybridization reaction of a probe nucleic acid immobilized on a substrate with a nucleic acid contained in a sample.

BACKGROUND ART

With the progression of the genome sequence project, the detection of particular genes on the genome, the analysis of SNPs, and expression analysis have received attention as post-genomic challenges. Therefore, analysis methods such as a hybridization method using a microarray (DNA chip) and an in situ hybridization method have become increasingly important as methods for detecting a target sequence in recent medical and molecular biological fields. In the microarray hybridization method, probe nucleic acids binding specifically to a target substance are immobilized on a substrate, and the presence or amount of the target substance in a sample is analyzed through the hybridization of the probe nucleic acids with the sample.

In general, these hybridization reactions are carried out by dropping a target nucleic acid-containing hybridization solution onto a substrate on which probe nucleic acids binding specifically to a target nucleic acid are immobilized.

This target nucleic acid is sometimes obtained in small amounts from a sample. For example, in gene examination for identifying pathogenic bacteria of bacteremia, the number of bacteria contained in blood is approximately several to several tens of cfu/mL. Thus, these examinations using hybridization are usually performed after nucleic acid amplification for increasing the amount of a target nucleic acid. Particularly, the polymerase chain reaction (PCR method) has often been used as an amplification reaction.

Thus, analysis combining nucleic acid amplification with the hybridization reaction has problems such as complicated handling of sample solutions and contamination. In this regard, Japanese Patent Application Laid-Open No. 2004-298017 has disclosed a solid phase probe array for reaction including plural reaction portions.

However, even more than contamination and complicated procedures, a further rapid reaction has been demanded in gene examination performed particularly in clinical fields.

In this regard, a technique for accelerating each reaction at nucleic acid amplification and at hybridization has been developed so far.

For example, in regard to more rapid nucleic acid amplification, Japanese Patent Application Laid-Open No. 2005-328709 has disclosed a method for performing high-speed PCR using heat-resistant DNA polymerase having a deoxyribonucleic acid synthesis rate of 100 bases/second or more.

Examples of more rapid hybridization reaction include a method performing agitation. For example, Japanese Patent No. 3746756 has disclosed an apparatus including an operation unit for stirring a sample solution, which causes a relative motion between a table member for holding a substrate on which a probe is immobilized and a plate member provided to form space to be filled with the sample solution.

An alternative method has also been disclosed which includes efficiently performing hybridization in a short time by transferring a nucleic acid for detection by use of dielectrophoresis. For example, Japanese Patent Application Laid-Open No. 2006-047153 has disclosed a method including hybridizing a nucleic acid for detection with a target nucleic acid by applying an electric field to an opposing electrode of a DNA chip having a detection portion including the opposing electrode capable of applying an electric field to a medium held in a hybridization chamber.

DISCLOSURE OF THE INVENTION

An object of the present invention is to provide a method and an apparatus for conducting examination in a short time in a gene examination method using conventional hybridization reaction.

To attain the object, the present invention provides a method for hybridizing a target nucleic acid contained in a sample solution with a probe nucleic acid capable of binding specifically to the target nucleic acid and immobilized on a substrate, characterized by including steps of: hybridizing the target nucleic acid with the probe nucleic acid; collecting the sample solution that has undergone the hybridization; amplifying the target nucleic acid contained in the collected sample solution; and hybridizing the amplified nucleic acid with the probe nucleic acid.

The present invention also provides an apparatus for hybridizing a target nucleic acid contained in a sample solution with a probe nucleic acid capable of binding specifically to the target nucleic acid and immobilized on a substrate, characterized by including: a reaction chamber for hybridizing the target nucleic acid with the probe nucleic acid; a collection system for collecting the sample solution within the reaction chamber; an amplification system for amplifying the target nucleic acid contained in the collected sample solution; and a supply system for supplying the amplified nucleic acid again to the reaction chamber.

The present invention further provides a reaction cartridge for hybridizing a target nucleic acid contained in a sample solution with a probe nucleic acid capable of binding specifically to the target nucleic acid and immobilized on a substrate, characterized by including: a reaction chamber for hybridizing the target nucleic acid with the probe nucleic acid; an amplification chamber for amplifying the target nucleic acid contained in the sample solution; and a flow channel for connecting the reaction chamber to the amplification chamber, wherein the reaction cartridge is constructed to simultaneously perform the hybridization reaction, the amplification reaction, and liquid transfer within the flow channel.

The hybridization method, the reaction cartridge, and the apparatus according to the present invention can increase the concentration of a target nucleic acid during hybridization reaction. This can improve hybridization reaction efficiency and perform hybridization more rapidly and more sensitively than conventional hybridization methods.

Further features of the present invention will become apparent from the following description of exemplary embodiments with reference to the attached drawings.

BRIEF DESCRIPTION OF THE DRAWING

FIG. 8 is a flow chart illustrating one example of the method of the present invention.

BEST MODES FOR CARRYING OUT THE INVENTION

Figure 1:
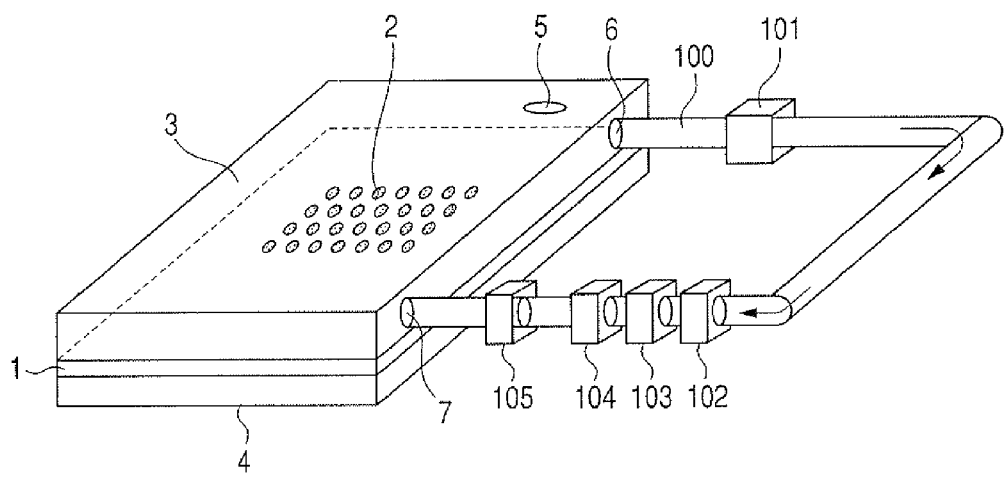
FIG. 1 is a schematic view illustrating one example of an apparatus suitable for carrying out the method of the present invention.

Prior to the detailed description of the present invention below, terms related to the present invention will be defined as follows:

Denaturation used herein refers to the breakdown of the double helix structure of a double-stranded nucleic acid and its dissociation into two single strands. Moreover, a denaturation temperature is defined as a temperature at which the double helix structure of a double-stranded nucleic acid is broken down and dissociated into two single strands. When a double-stranded DNA is heated to 90° C. or higher, changes in physical properties attributed to the structural change are observed. The denaturation temperature, in the narrow sense, is also defined as a median point of a temperature range causing the changes in physical properties. However, these changes in physical properties occur in a very narrow temperature range. Therefore, in the present invention, the denaturation temperature may also encompass a temperature of rising of the change.

A hybridization temperature refers to a temperature for causing the hybridization reaction. Suitable temperature conditions are set appropriately based on conditions such as the base length or sequence of a target nucleic acid and reagents used.

A probe is capable of binding specifically to a particular target and is often called a ligand. This probe encompasses oligonucleotides, polynucleotides, and other polymers. The probe may mean a probe molecule itself having probe functions, such as individual polynucleotide molecules, or may mean a population of probe molecules having the same probe functions, such as polynucleotides having the same sequences, which are immobilized in a dispersed state on carrier surface.

The probe adopted by the present invention is selected appropriately according to the purpose of use thereof. The probe suitable for carrying out a method of the present invention can be any of DNA, RNA, cDNA (complementary DNA), PNA (peptide nucleic acid), oligonucleotides, polynucleotides, other nucleic acids, and analogs thereof. These probes can be used in combination of two or more of them, if necessary.

Artificially synthesized oligo DNA, BAC DNA synthesized with vectors such as bacteria, cDNA, and so on are used as probe nucleic acids for a hybridization method. The suitable base length of the probe nucleic acid that can be used in the present invention is approximately 10 to 100 mer in terms of short-chain oligo DNA and approximately several kmer in terms of long-chain BAC DNA.

A DNA chip is a substrate (solid phase carrier) on which one to plural probe nucleic acids are immobilized. In general, the probe is often immobilized via a linker on a substrate. Poly-L-lysine has been well known to be utilized as a linker for an amino-modified oligonucleotide. In addition, a method has also been known which includes providing substrate surface with an amino group-reactive epoxy or carboxyl group (including activated one, if necessary). Alternatively, a mercapto group-modified oligonucleotide can be immobilized, for example, via a divalent reagent such as EMCS (N-(6-maleimidocaproyloxy) succinimide) on slide glass surface treated with an aminosilane coupling agent. In addition to the methods including binding a prepared probe nucleic acid onto a substrate, a method has also been practiced which includes synthesizing a nucleic acid on a substrate by a photolithography technique.

The substrate is often made of glass (e.g., quartz and borosilicate) or a resin and may be rendered porous. A substrate illustrated in FIG. 1 is in a plate form. However, the substrate of the present invention is not limited to this form and may be one forming a flow channel, or one in a filter form for passing a reaction solution therethrough, or a reeled thread on which plural probes are immobilized. Furthermore, the substrate may be constructed so that plural particulate substrates on which a probe nucleic acid is immobilized are incorporated in a chamber.

A temperature control system may be any system in any form as long as the system is a temperature control unit that can raise or lower the temperature of a reaction solution in a flow channel or chamber. For example, construction in which a heater or Peltier device is provided around a flow channel can be used as a temperature control system. The present invention encompasses a single temperature control system that sets the temperature of a reaction solution to a certain constant temperature and a single temperature control system that raises or lowers the temperature of a reaction solution to plural temperatures.

A chamber (reaction chamber, amplification chamber, hybridization chamber, etc.) described in the present invention is used in the broad sense. Specifically, the chamber is a reaction field for carrying out reaction and does not necessarily have to assume a structure like a reaction room. The present specification also encompasses, for example, reaction carried out in a whole or partial region on the flow channel.

A reaction cartridge described in the present invention refers to a small-size system in which a reaction chamber, a flow channel for supplying reagents thereto, and so on, necessary for reaction are accommodated in one case. The reaction cartridge may include necessary reagents. The reaction cartridge encompasses, for example, a chemical/biochemical analysis integration system in which operation sites such as liquid supply, mixing, reaction, and analysis are integrated on a chip about several cm per side, such as glass or silicon, as typified by μTAS (Micro Total Analysis System).

Hereinafter, a hybridization method according to the present invention will be described.

In conventional hybridization methods, a target nucleic acid is sufficiently amplified and then subjected to hybridization reaction. Therefore, the target nucleic acid insufficiently amplified at the amplification requires much time for the hybridization reaction and results in long examination.

Figure 7:
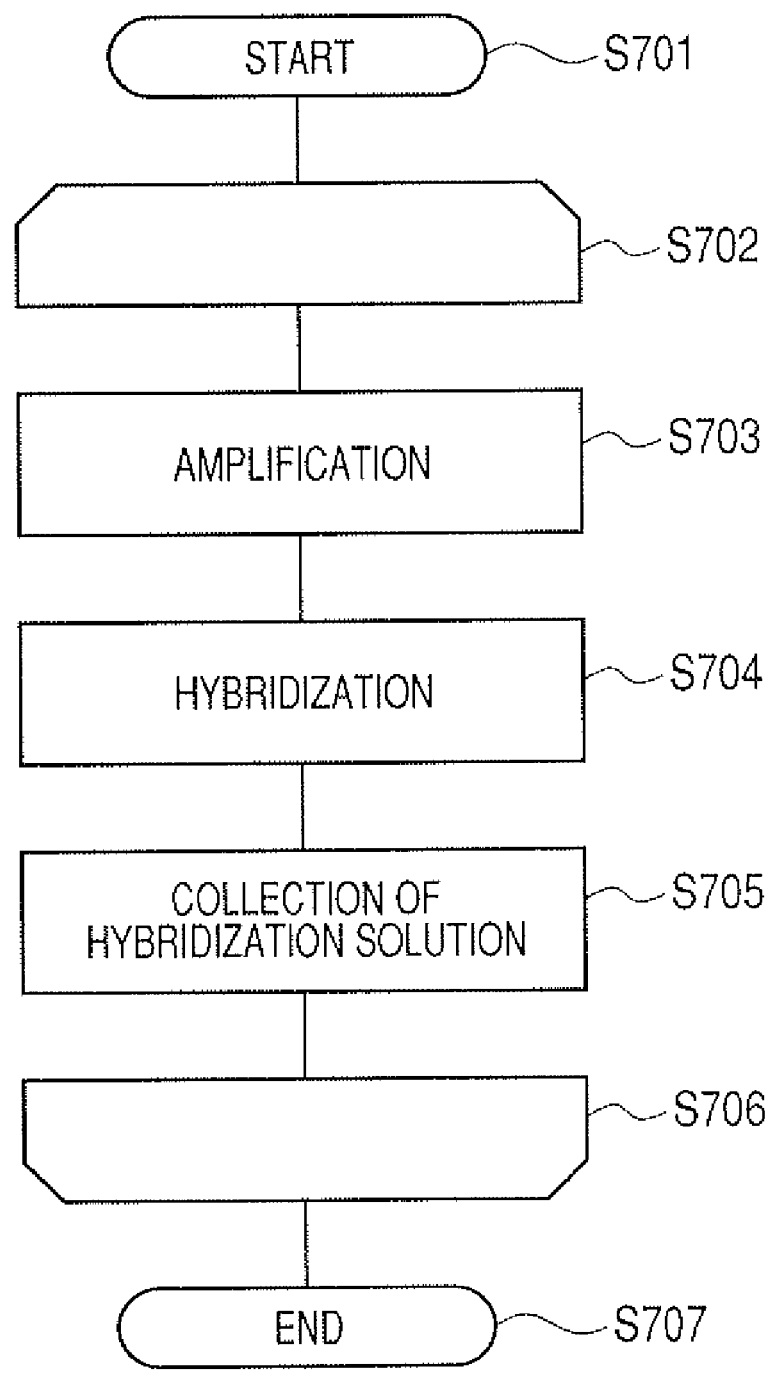
FIG. 7 is a flow chart illustrating one example of the method of the present invention.

In a hybridization method of the present invention, of course, a target nucleic acid may be amplified once (hereinafter, this amplification is referred to as preamplification) and subsequently subjected to hybridization, as in the conventional methods. In this case, as illustrated in the flow chart of FIG. 7, the target nucleic acid is amplified (S703) prior to hybridization. Various approaches have been known as methods for nucleic acid amplification. In general, a PCR method is often used. The PCR method includes: extension for synthesizing nucleic acids from a template nucleic acid and dNTP (deoxynucleotide) by use of an amplification enzyme;

denaturation in which the synthesized nucleic acids are dissociated; and annealing for hybridizing primers to the dissociated target nucleic acids. Amplification is usually achieved by repeating these operations. However, in the present invention, this amplification cycle may be performed once, and hybridization and subsequent amplification may be repeated, as described later. Alternatively, the amplification cycle may be repeated plural times, as in usual PCR, and then, subsequent hybridization may be carried out. The amplification method is not particularly limited as long as the amplification method can efficiently amplify the target nucleic acid.

The target nucleic acid thus amplified is hybridized with a probe on a solid phase carrier (S704). The hybridization solution containing the unreacted target nucleic acid is collected (S705). The collected solution is subjected to nucleic acid amplification (S703) again. This procedure is repeated plural times (S702, S706). Thus, even when the amount of the target nucleic acid contained in the initial hybridization solution is small due to insufficient amplification in preamplification, the target nucleic acid is hybridized while amplified and is therefore gradually increased in concentration, leading to rapid hybridization reaction.

Alternatively, the solution containing the preamplified target nucleic acid is added to a hybridization chamber and subjected to the hybridization of the target nucleic acid with the probe (S803), as illustrated in the flow chart of FIG. 8. The hybridization solution containing the unreacted target nucleic acid is collected (S804) and amplified (S805). The amplified solution is transferred to the hybridization chamber again and subjected to hybridization (S803). This procedure is repeated plural times (S802, S805). Thus, rapid hybridization reaction is achieved, as described above.

In this case, the target nucleic acid is reacted with the probe by the initial hybridization reaction and therefore reduced in amount in the sample solution. The target nucleic acid is synthesized with its complementary strand as a template. Therefore, amplification efficiency presents no problem even when the target nucleic acid is reacted with the probe at the initial and subsequent hybridizations and reduced in amount in the sample solution.

As described above, the target nucleic acid can be amplified even during hybridization. The target nucleic acid concentration becomes higher than that in conventional hybridization performed at a constant concentration of a target nucleic acid. Therefore, hybridization can be performed more rapidly and more sensitively. In some cases, preamplification can require a time shorter than that of conventional nucleic acid amplification performed prior to hybridization, or can be omitted.

Hereinafter, specific embodiments of a hybridization method, a reaction cartridge, and an apparatus according to the present invention will be described. However, the present invention is not intended to be limited to them.

(First Embodiment)

FIG. 1 is a schematic view illustrating one example of a suitable hybridization apparatus of the present invention. In FIG. 1, a substrate (DNA chip) 1 on which probes 2 are immobilized is mounted onto a temperature control system 4 for a hybridization chamber. A top board and so on is installed thereon to thereby form a hybridization chamber 3.

The chamber 3 may be in any shape and made of any material as long as the chamber has a shape that can retain a reaction solution on the substrate 1 and does not inhibit the reaction. If the chamber 3 is constructed so that the state of the substrate 1 is observed through the chamber 3, a material appropriate for the observation unit can be used.

A sample solution containing a target nucleic acid and reagents for amplification is injected from a sample solution injection port 5 by a method that is not illustrated in the drawings.

The temperature control system 4 for a hybridization chamber can control a temperature suitable for hybridization. For example, the temperature may be adjusted in the range of approximately 30° C. to 70° C. This temperature control system is controlled by a user or control apparatus by a method that is not illustrated in the drawings. The optimal value of a hybridization temperature differs depending on a denaturation temperature (Tm), a salt concentration, and other conditions. The optimal temperature may be selected according to a sample.

In this point of time, the target nucleic acid is contained in small amounts in the sample solution, often resulting in insufficient sensitivity in measurement. In such a case, the target nucleic acid must be amplified. Temperature and necessary reagents differ depending on an amplification method. Here, the amplification will be described by taking a PCR method as an example.

A flow channel 100 can connect an outlet 6 of the chamber 3 to an inlet 7 thereof and may be in any shape and made of any material as long as the flow channel does not influence the reaction. Depending on a material, the flow channel 100 can be surface-treated to prevent reagents such as enzymes and nucleic acids from being adsorbed thereon. Within the flow channel 100, a reaction solution is circulated by a liquid supply pump 101. The cross section of the flow channel 100 may be shaped differently in some sites to thereby adjust the flow rate of a reaction solution. Furthermore, the flow channel may also be constructed so that a reaction solution transiently stays therein by providing, in the flow channel, a buffer region that is not illustrated in the drawings.

First, a sample solution is collected into a first temperature control system 102 through the liquid supply pump 101. In this temperature control system, the sample solution is heated to a denaturation temperature of a double-stranded nucleic acid consisting of the target nucleic acid and its complementary strand or higher to thereby denature the double-stranded structure into single strands. For example, the temperature is selected in the range of, but not limited to, approximately 90° C. to 95° C. Alternatively, this procedure may be performed, if necessary.

The liquid supply pump 101 and the first temperature control system 102 are controlled by a user or control apparatus that is not illustrated in the drawings (hereinafter, the same holds true for other temperature control systems).

Subsequently, the sample solution is directed to a second temperature control system 103. In the second temperature control system 103, the temperature is adjusted to a temperature suitable for annealing primers for amplification with nucleic acids. For example, the temperature is selected in the range of, but not limited to, approximately 50° C. to 60° C.

Next, the sample solution is directed to a third temperature control system 104. In the third temperature control system 104, the primers are extended by use of heat-resistant DNA polymerase. In this procedure, the temperature differs depending on the enzyme and so on and is selected in the range of 68° C. to 72° C., for example, for the use of TaKaRa ExTaq (registered trademark, manufactured by Takara Bio).

Finally, the sample solution may be directed to a fourth temperature control system 105, if necessary. In the fourth temperature control system 105, the temperature is usually adjusted to almost the same temperature as that of the temperature control system 4 for a hybridization chamber. The fourth temperature control system is used for changing the sample temperature from the extension temperature to a temperature suitable for hybridization before the sample solution is directed onto the probes 2. This fourth temperature control system 105 can be substituted by the temperature control system 4 for a hybridization chamber and therefore, does not necessarily have to be provided therein.

When both strands of the double-stranded nucleic acid are amplified in extension reaction, two primers are generally added in equal amounts to the sample solution. In such a case, both the strands are amplified exponentially according to the number of heat cycles. However, the probe on the DNA chip is hybridized to one of sense and antisense strands of the nucleic acid as a target nucleic acid. Immediately after extension reaction, the sense and antisense strands are in a double-stranded form. For converting this double-stranded structure into single strands, a temperature control system for denaturation that is not illustrated in the drawings may be provided between the third temperature control system 104 and the fourth temperature control system 105. The temperature used in this temperature control system for denaturation is adjusted to a temperature equal to that of the first temperature control system 102. After denaturation, the solution must be directed to the hybridization chamber 3 in a short time as long as the temperature of the solution in the hybridization chamber 3 does not exceed the optimal temperature. This is because the target nucleic acid and its complementary strand contained in the sample solution are hybridized with each other prior to hybridization to the probes 2 on the substrate 1, resulting in reduction in the efficiency of reaction with the probes 2.

Alternatively, so-called asymmetric PCR including relatively increasing the amount of the target nucleic acid or amplifying only the target nucleic acid can be performed rather than performing denaturation. An asymmetric PCR method includes a method including differentiating the concentration of a primer for sense strand amplification from that of a primer for antisense strand amplification and a method using only one primer.

In the former method, for example, the ratio in concentration between the primer for sense strand amplification and the primer for antisense strand amplification is set to 100:1. In the initial stage of heat cycles, both the sense and antisense strands are amplified exponentially in almost equal amounts. However, in the latter part of the heat cycles, a smaller amount of the primer (here, the primer for antisense strand amplification) is nearly exhausted, and a strand (here, the antisense strand) amplified therefrom is gradually decreased in amplification amount. Thus, the amount of another strand (here, the sense strand) hybridized to the probe 2 is rendered significantly lager than that of the strand (here, the antisense strand) not hybridized to the probe 2. Thus, the temperature control system for denaturation that is not illustrated in the drawings does not have to be provided downstream of the third temperature control system 104 for extension reaction.

An alternative suitable method, as disclosed in Japanese Patent Application Laid-Open No. 2005-000162, can also be used which includes performing PCR amplification reaction using two primers flanking a base sequence region to be amplified, which have different melting temperatures (Tm values) under PCR reaction conditions.

The asymmetric PCR method is not limited to the methods described above, and other asymmetric PCR methods may be adopted.

In amplification, labeling of some sort can be used for easily observing the DNA chip. In general, a method using a primer labeled at its end with a fluorescent dye typified by Cy3 and Cy5 and so-called incorporation labeling including synthesizing a fluorescently labeled nucleic acid by mixing deoxynucleotide (dNTP) with fluorescently labeled dNTP are used. Furthermore, a method using a fluorescent intercalator typified by SYBR (U.S. registered trademark) Green I rather than labeling the target nucleic acid itself can also be used. Here, the fluorescent label is taken as an example. However, other labels used in DNA chip observation may be used.

In FIG. 1, the temperature control systems 102, 103, 104, and 105 are illustrated at the same size. However, the sizes of the temperature control systems can be rendered different. For example, a PCR amplification kit of TaKaRa ExTaq (registered trademark) involves denaturation at 98° C. for 10 seconds, annealing at 55° C. for 30 seconds, and extension reaction at 72° C. for 1 minute in the standard protocol for amplifying 1-kbp DNA. Thus, the ratio in length among the first temperature control system 102, the second temperature control system 103, and the third temperature control system 104 is set to 1:3:6.

Time is adjusted by the width of the flow channel and the speed of the liquid supply pump 101.

The target nucleic acid thus amplified is returned to the hybridization chamber 3 and hybridized again with the probe 2.

This series of operations are repeated to thereby carry out hybridization during nucleic acid amplification, achieving more rapid hybridization.

After the reaction is performed by a predetermined number of cycles or for a predetermined time, the probe and the unreacted reagents are washed away by a method that is not illustrated in the drawings, and the DNA chip is dried by a method that is not illustrated in the drawings. The DNA chip thus obtained that has undergone reaction is observed with an existing measurement apparatus. For example, when the target nucleic acid is labeled with a fluorescent dye, an existing microarray scanner such as a GenePix (U.S. registered trademark) microarray scanner (manufactured by Axon instruments) may be used.

Figure 4:
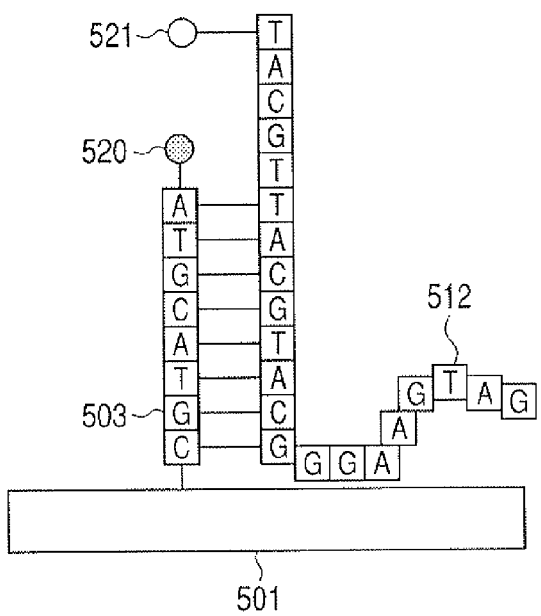
FIG. 4 is a schematic view illustrating one example of a detection method used in the method of the present invention.

Next, detection using FRET (Fluorescence resonance energy transfer) will be described with reference to FIG. 4. A probe nucleic acid 503 is immobilized on a substrate 501. The probe nucleic acid 503 has a nucleic acid sequence binding specifically to a target nucleic acid 512. The present embodiment is characterized by a first dye 520 used as a label for the probe nucleic acid 503 and a second dye 521 used as a label for the target nucleic acid 512. The first dye 520 and the second dye 521 are a pair of fluorescent dyes that can cause FRET between them. The first dye 520 and the second dye 521 may be bound to any portion of the probe nucleic acid 503 and the target nucleic acid 512, respectively, and must be placed at a distance that can cause the FRET phenomenon between them during binding. FRET is a phenomenon of excitation energy transfer from a certain fluorescent molecule (donor molecule) to another molecule (acceptor molecule). The FRET phenomenon occurs only when the donor molecule and the acceptor molecule are located close to each other (usually, within 50 to 100 Å). Therefore, fluorescence intensity observed from outside differs according to the distance between these compounds. As illustrated in FIG. 4, the first dye 520 is bound as a donor dye to the probe nucleic acid 503, while the second dye 521 is bound as an acceptor dye to the target nucleic acid 512. As a result, the FRET phenomenon occurs only during the binding of the probe nucleic acid 503 and the target nucleic acid 512 and emits fluorescence. The target nucleic acid unbound with the probe nucleic acid 503 does not cause the FRET phenomenon and therefore, does not emit fluorescence. Accordingly, the influence of the unbound target nucleic acid can be eliminated even in a reaction solution containing the labeled target nucleic acid.

Therefore, the binding of the probe nucleic acid and the target nucleic acid can be detected accurately.

Figure 5:
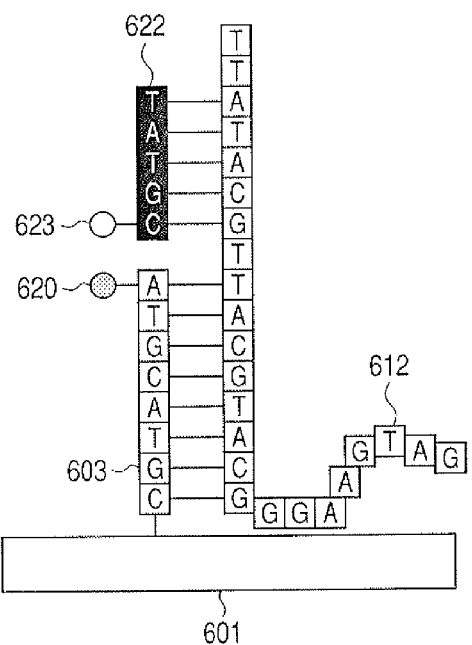
FIG. 5 is a schematic view illustrating one example of a detection method used in the method of the present invention.

Furthermore, another hybridization detection method of the present invention will be described with reference to FIG. 5. A probe nucleic acid 603 is immobilized on a substrate 601. The probe nucleic acid 603 has a nucleic acid sequence binding specifically to a target nucleic acid 612. A labeled probe 622 is constructed to bind specifically to a site located in proximity to the probe nucleic acid 603-binding site of the target nucleic acid 612. The present method is characterized by a first dye 620 used as a label for the probe nucleic acid 603 and a third dye 623 used as a label for the labeled probe 622. The first dye 620 and the third dye 623 are a pair of fluorescent dyes that can cause FRET between them. The first dye 620 and the third dye 623 may be bound to any portion of the probe nucleic acid 603 and the labeled probe 622, respectively, and must be placed at a distance that can cause the FRET phenomenon between them during binding. The FRET phenomenon occurs between the first dye 620 and the third dye 623 only during the binding of the probe nucleic acid 603 and the target nucleic acid 612 and emits fluorescence. When the target nucleic acid 612 is unbound with the probe nucleic acid 603, the FRET phenomenon does not occur. Therefore, no fluorescence is emitted. Accordingly, the target nucleic acid does not have to be labeled, and the binding of the probe nucleic acid and the target nucleic acid can be detected accurately.

Next, a solution for a PCR method used as an amplification method will be described. The target nucleic acid is prepared into an appropriately formulated hybridization solution containing reagents necessary for PCR. The PCR reagents are those utilized in PCR reaction and contain, for example, the followings:
1. primer DNAs binding specifically to both ends of the amplification site of a target sequence;
2. DNA polymerase synthesizing DNA complementary to the target sequence from the primers bound with the target nucleic acid;
3. a variety of nucleotides (e.g., dNTP) necessary for DNA synthesis;
4. salts such as magnesium chloride and potassium chloride; and
5. buffers such as Tris.

As an example, the composition of a hybridization solution includes buffers, a denaturant such as formamide, and a defoaming agent. The hybridization solution can be formulated not to inhibit the function of the PCR reagents. Alternatively, labeled primers, an intercalator such as SYBR (U.S. registered trademark) Green, and labeled nucleotides are sometimes contained for hybridization detection.

(Second Embodiment)

Figure 2:
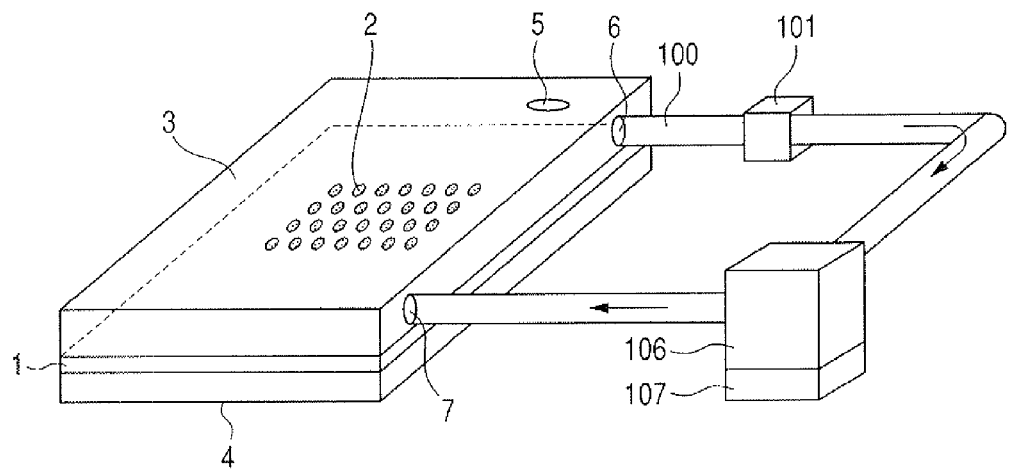
FIG. 2 is a schematic view illustrating one example of an apparatus suitable for carrying out the method of the present invention.

Next, an alternative embodiment of the present invention will be described with reference to FIG. 2. In FIG. 2, amplification is not performed within a flow channel but performed in an amplification chamber 106 provided separately from a hybridization chamber 3.

A portion of a sample solution injected is collected into the amplification chamber 106 by use of a liquid supply pump 101. In the amplification chamber 106, a temperature control system 107 for an amplification chamber is installed and can heat or cool the sample solution in the amplification chamber 106 to any temperature. In this procedure, the remaining sample solution is used in hybridization reaction within the hybridization chamber 3 or stays within the flow channel.

When a PCR method is used in amplification reaction, the sample solution that has entered the amplification chamber 106 is subjected to a heat cycle using temperatures and times suitable for denaturation, annealing, and extension, as in the first embodiment.

The sample solution amplified through one or plural heat cycles is directed again to the hybridization chamber 3 by actuating the liquid supply pump 101. In this procedure, the remaining sample solution is directed to the amplification chamber 106 and subjected to amplification reaction.

(Third Embodiment)

Figure 3:
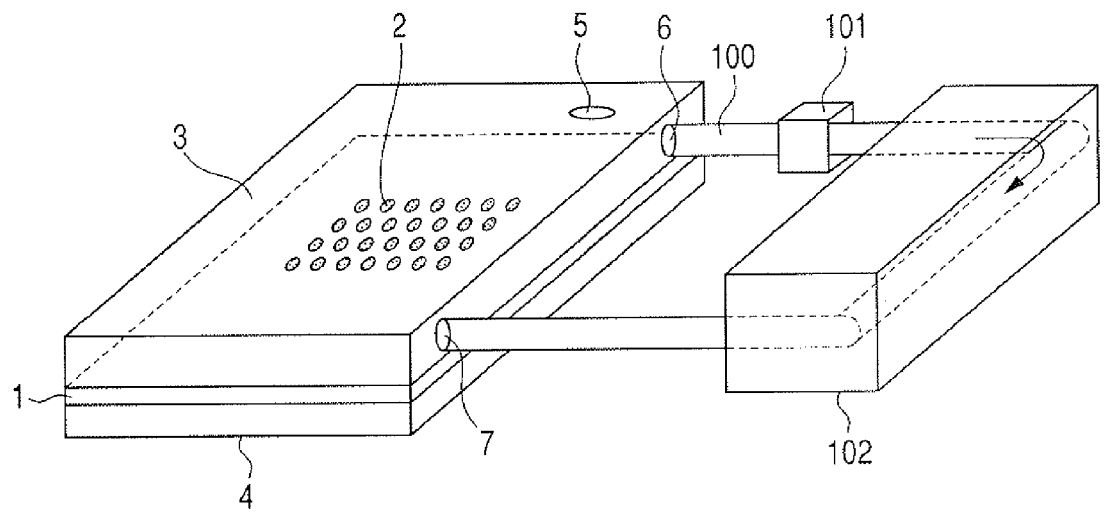
FIG. 3 is a schematic view illustrating one example of an apparatus suitable for carrying out the method of the present invention.

Next, an alternative embodiment of the present invention will be described with reference to FIG. 3. FIG. 3 illustrates a single temperature control system. A hybridization solution collected from an outlet 6 is sent to a temperature control system 102 through a liquid supply pump 101. The hybridization solution is subjected to one or plural heat cycles while passing through the temperature control system 102. Specifically, the hybridization solution is subjected to denaturation, annealing, and extension once to multiple times, from the outlet 6 to an inlet 7. The sequence of temperatures and times thereof is as shown in the first embodiment.

The liquid supply pump 101 may be operated continuously or may be stopped in some cases. When the liquid supply pump is operated continuously, the hybridization solution is sometimes added to the temperature control system 102 during the heat cycle, for example, at a point of time when an annealing temperature is selected. However, those skilled in the art can understand that this addition during the heat cycle presents no problem.

(Fourth Embodiment)

Figure 6:
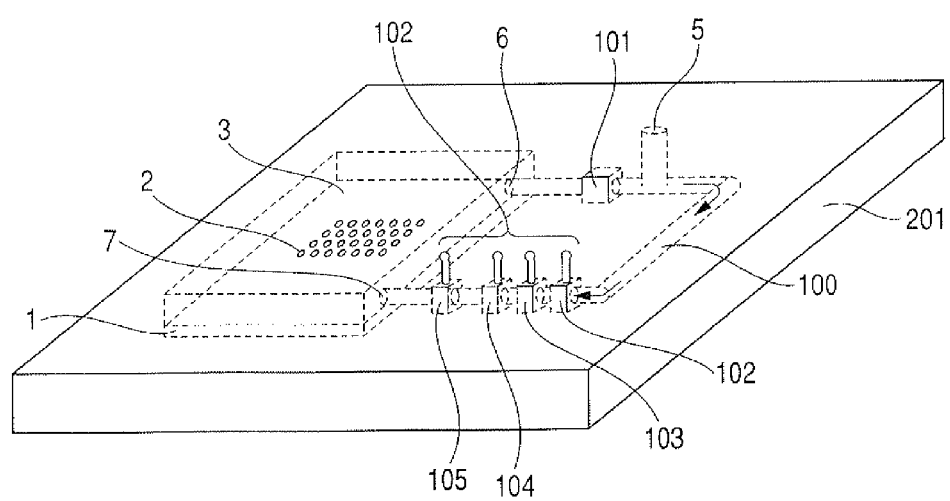
FIG. 6 is a schematic view illustrating one example of a cartridge suitable for carrying out the method of the present invention.

Next, a reaction cartridge 201 will be illustrated as a fourth embodiment in FIG. 6, in which the reaction chamber portion in the apparatus constructions of the embodiments described above is changed to a cartridge.

Specifically, a cartridge on which probes 2 capable of binding specifically to a target nucleic acid are immobilized is constructed to include a reaction chamber 3 for accommodating the probe nucleic acid therein, a sample injection port 5 for supplying a target nucleic acid-containing sample solution to the reaction cartridge 201, a flow channel 100 for collecting the sample solution supplied to the hybridization chamber 3, and temperature control systems 102, 103, 104, and 105 for amplifying the target nucleic acid. These temperature control systems 102, 103, 104, and 105 can be controlled through control terminals 202 from a control apparatus that is not illustrated in the drawings.

The embodiment illustrated in FIG. 6 is generally the same as the first embodiment. However, because members with which the sample solution comes into contact are included in a hermetically sealed cartridge, this embodiment can preferably prevent contamination with other sample solutions and contaminants.

In the embodiment of FIG. 6, the temperature control systems 102, 103, 104, and 105 involved in amplification are made of a member with good heat conductivity, such as a metal, and the member covers the flow channel or is in contact with the flow channel. Heat can be applied from outside to the temperature control terminals 202 to thereby adjust the temperature of the sample solution within the flow channel. In this case, the distance of each of the temperature control systems 102, 103, 104, and 105 from the corresponding temperature control terminal 202 may be short for fast and accurate heat conduction.

A temperature control device such as a very small heater or a Peltier device may be provided within the cartridge and constructed to control the temperature by supplying a power thereto from the corresponding temperature control terminal 202.

Such a cartridge can be produced by those skilled in the art by using resin molding or μTAS techniques.

The solution containing the target nucleic acid and reagents necessary for amplification is injected from the sample solution injection port 5. The target nucleic acid is amplified by the temperature control systems 102, 103, 104, and 105 according to the flow described in FIG. 7. The amplified target nucleic acid is sent to the hybridization chamber 3 through the liquid supply pump 101 and hybridized with the probe 2. The unreacted target nucleic acid and a complementary strand of the target nucleic acid are amplified again by the temperature control systems 102, 103, 104, and 105. This procedure is repeated.

The present invention also encompasses the constructions of a cartridge including plural pieces of the reaction system described above and an apparatus that can hold plural cartridges, for treating plural samples by one operation.

Fifth Embodiment (1) Substrate Preparation

A 1×3 inch-square synthetic quartz glass substrate is washed by brush washing with pure water, rinsing with pure water, ultrasonic washing with an alkaline detergent, rinsing with pure water, ultrasonic washing with pure water, rinsing with pure water, and drying by nitrogen blow to prepare a quartz glass substrate having clean surface.

An aminosilane coupling agent (trade name: KBM-903; manufactured by Shin-Etsu Chemical) is dissolved at a concentration of 1% by weight in water. The methoxy group is hydrolyzed by stirring for 30 minutes. The slide glass is dipped in this aqueous solution for 30 minutes and then taken out thereof. The slide glass is washed with pure water and subjected to baking treatment in an oven at 120° C. for 1 hour. If a vacuum oven is used, the slide glass may be baked for approximately 5 minutes.

Subsequently, EMCS is dissolved at a concentration of 0.3 mg/ml in 1,4-dioxane.

The baking-treated amino group-introduced quartz glass substrate is dipped in the EMCS solution at room temperature for 2 hours to introduce a maleimide group onto the surface. After the treatment with the EMCS solution, the substrate is washed and dried under a nitrogen atmosphere.

(2) Synthesis of Probe DNA

In the present embodiment, probes used are single-stranded nucleic acids that have a base sequence complementary to the whole or a partial sequence of a target nucleic acid to be detected and allow for the detection of the target nucleic acid through specific hybridization with the base sequence of the target nucleic acid. The single-stranded nucleic acid of SEQ ID NO: 1 is synthesized with an automatic DNA synthesizer. A mercapto group is introduced into the end of the single-stranded DNA of SEQ ID NO: 1 by using Thiol-Modifier (manufactured by Glen Research) during its synthesis with the automatic DNA synthesizer. Subsequently, after usual deprotection, the DNA is collected and purified by high-performance liquid chromatography.

The probe nucleic acid of SEQ ID NO: 1 is a portion encoding the 16s RNA of an *Enterobacter cloacae* strain disclosed in Japanese Patent Application Laid-Open No. 2007-014351.

5'HS- GTAGCACAGAGAGCTTGCTCTCG 3'   (SEQ ID NO: 1)

(3) Immobilization of Probe

The DNA fragments (SEQ ID NO: 1) synthesized in the paragraph (2) are dissolved at a concentration of approximately 9 μM in an aqueous solution containing 15% glycerin, 15% urea, 9% diethylene glycol, and 0.01% acethylene alcohol (trade name: Acetylenol E100; manufactured by Kawaken Fine Chemicals).

The aqueous solution containing these DNA fragments is spotted by an ink jet method onto each slide glass prepared by the method of the paragraph (1). The slide glass is further left at room temperature for 30 minutes and washed with a 1 M NaCl/50 mM phosphate buffer solution (pH 7.0).

Subsequently, the probe-immobilized slide glass is blocked by dipping the slide glass at a room temperature for 1 hour in a solution containing BSA (Bovine Serum Albumin Fraction V; manufactured by Sigma) dissolved at a concentration of 1% in 100 mM NaCl/10 mM Phosphate Buffer.

After the completion of blocking, the slide glass is washed with 2×SSC solution (300 mM NaCl, 30 mM Sodium Citrate (trisodium citrate dihydrate, $C_6H_5Na_3 \cdot 2H_2O$), pH 7.0) containing 0.1% SDS (sodium dodecyl sulfate), then rinsed with pure water, and dried by spin drying.

(4) Preparation of PCR Primer for Sample Amplification

Primers used are nucleic acid sequences shown in Table 1 as PCR primers for 16s rRNA gene (target gene) amplification for pathogenic bacterium detection disclosed in Japanese Patent Application Laid-Open No. 2007-014351.

TABLE 1

|  | Primer No. | SEQ ID NO | Sequence |
|---|---|---|---|
| Forward Primer | F-1 | 2 | 5' GCGGCGTGCCTAATACATGCAAG 3' |
|  | F-2 | 3 | 5' GCGGCAGGCCTAACACATGCAAG 3' |
|  | F-3 | 4 | 5' GCGGCAGGCTTAACACATGCAAG 3' |
| Reverse Primer | R-1 | 5 | 5' ATCCAGCCGCACCTTCCGATAC 3' |
|  | R-2 | 6 | 5' ATCCAACCGCAGGTTCCCCTAC 3' |
|  | R-3 | 7 | 5' ATCCAGCCGCAGGTTCCCCTAC 3' |

The primers shown in this table are purified by high-performance liquid chromatography (HPLC) after synthesis. These three Forward Primers are mixed and dissolved at each final primer concentration of 0.2 pmol/μl in a TE buffer solution. Moreover, these three Reverse Primers are mixed and dissolved at each final primer concentration of 10 pmol/μl in a TE buffer solution.

(5) Culture of Microorganism

First, an *Enterobacter cloacae* standard strain (ATCC13047) is cultured according to a standard method. This microorganism culture solution is collected in an amount of 1.0 ml (OD600=0.7) into a 1.5-ml microtube. The bacterial cells are collected by centrifugation (8500 rpm, 5 min., 4° C.). Next, the supernatant is discarded, and 300 μl of Enzyme Buffer (50 mM Tris-HCl, pH 8.0, 25 mM EDTA) is then added to the bacterial cells. The bacterial cells are resuspended with a mixer. The resuspended bacterial solution is subjected again to centrifugation to collect bacterial cells (8500 rpm, 5 min., 4° C.). The supernatant is discarded, and an enzyme solution described below is then added to the collected bacterial cells. The bacterial cells are resuspended with a mixer.

Lysozyme 50 μl (20 mg/ml in Enzyme Buffer)
N-Acetylmuramidase SG 50 μl (0.2 mg/ml in Enzyme Buffer)

Next, the bacterial solution resuspended by the addition of the enzyme solution is left standing for 30 minutes within an incubator set at 37° C. to perform the lysis treatment of the cell walls.

(6) Genome DNA Extraction

Microorganism Genome DNA extraction shown below is carried out with a nucleic acid purification kit (MagExtractor-Genome-; manufactured by TOYOBO).

Specifically, 750 µl of a lysis/adsorption solution and 40 µl of magnetic beads are first added to the pretreated microorganism suspension and vigorously stirred for 10 minutes with a tube mixer (Step 1).

Next, the microtube is loaded in a separation stand (Magical Trapper) and left standing for 30 seconds to gather the magnetic particles onto the wall surface of the tube. The supernatant is discarded with the tube loaded in the stand (Step 2).

Next, after the addition of 900 µl of washing solution, the mixture is stirred for approximately 5 seconds with a mixer to perform resuspension (Step 3).

Next, the microtube is loaded in a separation stand (Magical Trapper) and left standing for 30 seconds to gather the magnetic particles onto the wall surface of the tube. The supernatant is discarded with the tube loaded in the stand (Step 4).

Second washing is performed by repeating the steps 3 and 4 (Step 5). Then, after the addition of 900 µl of 70% ethanol, the mixture is stirred for approximately 5 seconds with a mixer to perform resuspension (Step 6).

Next, the microtube is loaded in a separation stand (Magical Trapper) and left standing for 30 seconds to gather the magnetic particles onto the wall surface of the tube. The supernatant is discarded with the tube loaded in the stand (Step 7).

Second washing with 70% ethanol is performed by repeating the steps 6 and 7 (Step 8). Then, after the addition of 100 µl of pure water to the collected magnetic particles, the mixture is stirred for 10 minutes with a tube mixer (Step 9).

Next, the microtube is loaded in a separation stand (Magical Trapper) and left standing for 30 seconds to gather the magnetic particles onto the wall surface of the tube. The supernatant is collected into a new tube with the tube loaded in the stand.

(7) Examination of Collected Genome DNA

The collected microorganism (Enterobacter cloacae strain) Genome DNA is subjected to agarose electrophoresis and absorbance measurement at 260/280 nm according to a standard method to test the quality (the amount of contaminating low-molecular-weight nucleic acids and the degree of degradation) and collected amount thereof. Degradation and rRNA contamination are not observed in the Genome DNA thus collected. The collected Genome DNA is dissolved at a final concentration of 1 ng/µl in a TE buffer solution.

The obtained Genome DNA may be preamplified by a known method such as PCR, if necessary.

(8) Preparation of Reaction Cartridge

A polyolefin-made top board having a top board and a flow channel is bonded to the DNA chip prepared in the paragraph (3) to prepare a hybridization chamber. This hybridization chamber has a size of 5 mm×10 mm×0.5 mm.

Moreover, the hybridization chamber is provided with a sample solution injection port for injecting a sample solution and a washing solution discharge port (2 mm each in diameter) and with an outlet and an inlet (both, 2.4 mm in diameter) for a sample solution. A tube of 0.8 mm in interior diameter and approximately 20 cm in length is connected between the outlet and the inlet. A unit for squeezing the tube in one direction is provided as a liquid supply pump in a portion of the tube. Moreover, four heaters in a plate form of 4 cm in length are immobilized on the tube (approximately 1 cm space is provided between the heaters for avoiding heat interference).

A heater is installed on the back side of the DNA chip for adjusting the temperature of a sample solution within the hybridization chamber.

Each of the heaters is provided with a K-type thermocouple to allow for temperature measurement.

The apparatus thus prepared has a volume of approximately 125 µL.

(9) Preparation of Sample Solution

Solutions having the composition shown in Tables 2 and 3 are prepared.

TABLE 2

| | |
|---|---|
| Premix PCR Reagent (manufactured by Takara Bio, ExTaq) | 62 µL |
| Template Genome DNA | 5 µL |
| Forward Primer mix prepared in (4) | 5 µL |
| Reverse Primer mix prepared in (4) | 5 µL |
| Cy3-dUTP (1 mM) | 5 µL |
| $H_2O$ | 43 µL |
| Total | 125 µL |

TABLE 3

| | |
|---|---|
| Premix PCR Reagent (manufactured by Takara Bio, ExTaq) | 62 µL |
| Forward Primer mix prepared in (4) | 5 µL |
| Reverse Primer mix prepared in (4) | 5 µL |
| Cy3-dUTP (1 mM) | 5 µL |
| $H_2O$ | 48 µL |
| Total | 125 µL |

(10) PCR & Hybridization

The heater for a hybridization chamber is set to 45° C.; the heater for denaturation is set to 92° C.; the heater for annealing is set to 55° C.; and the heater for extension is set to 72° C.

The sample solution prepared in the paragraph (9) is injected from the sample solution injection port. The liquid supply pump is controlled to send the sample solution at a flow rate of 0.45 µL/sec.

Two hours after start, the inlet and the outlet are closed. The heater installed in the back side of the DNA chip is removed, and a heat block set at 25° C. is installed therein instead of the heater to cool the hybridization solution. Then, 1 mL of 2×SSC/0.1% SDS mixed solution and 1 mL of 2×SSC are injected from the sample solution injection port to wash the DNA chip.

Subsequently, the top board is removed. The DNA chip is washed with pure water and dried by spin drying.

(11) Fluorescence Measurement

The DNA chip after the completion of the hybridization reaction is subjected to fluorescence measurement using a fluorescence detection apparatus (e.g., manufactured by Axon, GenePix 4000B).

A method using the apparatus and the reaction cartridge of the embodiments described above amplifies a target substance, with the progress of reaction. Therefore, the method requires a shorter time for hybridization reaction than that of conventional hybridization methods.

The present invention is not limited to the above embodiments and various changes and modifications can be made within the spirit and scope of the present invention. Therefore to apprise the public of the scope of the present invention, the following claims are made.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-201716, filed Aug. 2, 2007, which is hereby incorporated by reference herein in its entirety.

The invention claimed is:

1. A method for hybridizing a target nucleic acid contained in a sample solution with a probe nucleic acid capable of binding specifically to the target nucleic acid and immobilized on a substrate, comprising steps of:
hybridizing the target nucleic acid with the probe nucleic acid;
collecting the sample solution that has undergone the hybridization to collect the target nucleic acid which is not hybridized;
amplifying the target nucleic acid contained in the collected sample solution; and
hybridizing the amplified nucleic acid with the probe nucleic acid.

2. The method according to claim 1, wherein the sample solution further contains a complementary strand of the target nucleic acid, and that the amplification step includes asymmetric amplification of the target nucleic acid and the complementary strand.

3. The method according to claim 1, wherein the amplification step includes polymerase chain reaction (PCR).

4. The method according to claim 1, further comprising, prior to the hybridization step, a denaturation step in which the sample solution is heated to a temperature above denaturation temperatures (Tm) of the target nucleic acid and a complementary strand of the target nucleic acid.

5. The method according to claim 1, wherein the steps are performed in a reaction cartridge comprising:
   a reaction chamber for hybridizing the target nucleic acid with the probe nucleic acid;
   an amplification chamber for amplifying the target nucleic acid contained in the sample solution; and
   a flow channel for connecting the reaction chamber to the amplification chamber.

6. The method according to claim 1, wherein the flow channel comprises:
   a first flow channel for transferring the sample solution from the reaction chamber to the amplification chamber; and
   a second flow channel for transferring the sample solution from the amplification chamber to the reaction chamber,
   wherein the sample solution is circulated in the reaction chamber and the amplification chamber via the first flow channel and the second flow channel.

7. The method according to claim 1, wherein the collecting, the amplifying, and the further hybridizing are repeatedly performed after hybridizing the target nucleic acid with the probe nucleic acid.

* * * * *